United States Patent [19]
Knudson et al.

[11] 4,313,442
[45] Feb. 2, 1982

[54] ATRIAL RATE SENSITIVE CARDIAC PACER APPARATUS

[75] Inventors: Mark B. Knudson, Arden Hills; David C. Amundson, St. Paul, both of Minn.

[73] Assignee: Cardiac Pacemakers, Inc., St. Paul, Minn.

[21] Appl. No.: 170,947

[22] Filed: Jul. 21, 1980

[51] Int. Cl.³ .............................................. A61N 1/36
[52] U.S. Cl. ......................................... 128/419 PG
[58] Field of Search ................................. 128/419 PG

[56] References Cited
U.S. PATENT DOCUMENTS

3,693,626 9/1972 Cole .......................... 128/419 PG
4,009,721 3/1977 Alcidi ........................ 128/419 PG
4,091,817 5/1978 Thaler ....................... 128/419 PG Primary Examiner—William E. Kamm
Attorney, Agent, or Firm—Orrin M. Haugen; Thomas J. Nikolai

[57] ABSTRACT

An electrical pacer device which responds to cardiac demand so as to alter the cardiac output in a fashion to satisfy that demand. Changes in the fundamental period of the atrial electrical cycle are detected and averaged over a predetermined time interval and the resulting control signal is used to raise and lower the ventricular heart rate to increase and decrease the foresaid cardiac output. At the same time, means are provided for continuously driving the ventricular rate toward a predetermined lower rate (the at rest rate) on a time cycle which is significantly longer than the above-mentioned predetermined time interval.

5 Claims, 5 Drawing Figures

ATRIAL RATE SENSITIVE CARDIAC PACER APPARATUS

BACKGROUND OF THE INVENTION

I. Field of the Invention

This invention relates generally to cardiac pacer apparatus and more specifically to an improved cardiac pacer system which is responsive to the metabolic needs of the body and which optimizes cardiac output (blood flow) to suit those metabolic needs.

II. Discussion of the Prior Art

The human body can be viewed as a machine that is used by the mind to allow it to function in the physical world. It is started at conception and continues running until death, and like any machine, it requires energy to operate. The amount of energy required varies from "idle" when sleeping to "full throttle" during periods of maximum exertion and this energy is supplied through the blood stream. The heart, which is the pump for this system, must maintain this flow of energy so as to equal that required by the body during any given condition, such as during periods of sleep or during exercise.

In a normal heart, cardiac demand controls the cardiac output (blood flow rate) by virtue of the conduction of electrical impulses from the SA node to the AV node and from there down the bundle of His which passes to the ventricular septum, where it divides into two large bundle branches which supply both ventricles. Each branch spreads along the endocardial surface of the septum to the apex of the heart and then turns upward over the lateral wall of each ventrical. The Purkinje fibers of the AV bundle enter the ventricular walls and finally fuse with the heart muscle fibers and, in this way, each muscle fiber receives the impulse. When conduction system failures occur, the AV trigger signal arriving from the atrium is impacted and as a result, cardiac demand does not effectively control the cardiac output.

Prior art pacemakers attempt to replace the defective conduction system by establishing an artificially fixed heart rate to control a pulse generator for stimulating the ventricles. The heart rate is set sufficiently high to supply enough cardiac output to allow body maintenance as well as enough reserve to allow useful work. So-called-P-synchronous prior art pacer systems attempt to use the AV trigger from the atrium to alter the heart rate so as to allow the cardiac output to better match cardiac demand. P-synchronous pacer devices have not been altogether successful in that the atrial electrical activity for a cardiac system, while containing the information concerning cardiac demand, is not a precise system and like most biological systems, it is very difficult to measure atrial trigger signals with a high degree of accuracy and reliability. Most prior art pacemaker systems, such as the P-synchronous system, attempt to duplicate the very complex function of the cardiac electrical system. However, this tends to duplicate the very same problems that the P-synchronous system is intended to correct, primarily because of improper and imperfect signal sensing, detecting, processing and controlling.

In accordance with the teachings of the present invention, the problem of defective conduction of atrial trigger signals to the ventrical is approached from the standpoint of correcting the intent of the cardiac output and cardiac demand relationship instead of attempting to reproduce the rather complex control system within the heart itself. In that the atrial electrical activity contains the information concerning cardiac demand and since this information is directly related to the P-wave rate within this activity, in accordance with the present invention, the ventricular pacing rate is controlled as a function of detected changes of the P-wave rate.

SUMMARY OF THE INVENTION

In accordance with the present invention, a control circuit is provided for a conventional demand, R-wave inhibited, ventricular pacer whereby the pacer pulse rate of that device is controlled as a function of changes in the detected P-wave rate. A suitable lead having a stimulating electrode adapted to abut the apex of the ventricle and having further sensing electrodes disposed proximally of the tip or stimulating electrode so as to be disposed near the upper right wall of the atrium for sensing P-wave activity is coupled to the electronics package. The signals picked up at the sensing electrodes, which may include P-waves, R-waves, T-waves, muscle artifacts as well as noise, are applied to a P-wave detector which serves to filter and shape the incoming signals and to discriminate against all but the P-wave signals. Furthermore, since the cardiac system is not working properly, atrial flutter, premature atrial contractions (PAC's) and other anomalies of the atrium may be present. However, these anomalies, though not normal, still contain the information concerning the cardiac demand and the rate of these latter signals will vary according to that demand. The control circuit of the present invention extracts the change in the rate of these signals and uses this rate change to develop a control signal for the conventional demand/inhibit pulse generator driving the heart through the ventricular stimulating pulses applied to the heart by way of the stimulating tip electrode.

The signal applied to the demand/inhibit pacemaker to control the ventricular stimulating rate in accordance with cardiac demand in a manner similar to normal physiological control must accomplish two things.

(1) The actual ventricular stimulating rate must be raised and lowered by the cardiac demand signal, but must not go below the lowest allowable pacing rate and this rate must not be changed abruptly, but instead, over a physiologically compatible time, typically one to three minutes in the normal cardiac system.

(2) Any rise in the heart rate should be sufficiently long to sustain physical activity until the activity is completed, but not allow that activity to continue past the point of serious fatigue. This time in the normal cardiac system is approximately 20 to 40 minutes.

In the pacer control device of the present invention the first condition, that of raising and lowering the heart rate, is accomplished by coupling the output from the P-wave detector circuit to a P-wave averaging circuit in which small quantities of electrical charge, one increment for each detected P-wave, are summed in an integrating capacitor which is arranged to lose its charge with a time constant of approximately 30 seconds, thus producing a voltage related to the number of P-waves sensed and detected over the preceding approximately 1.5 minutes of any given time. The averaging circuit is designed to have a dynamic range from 0 P-waves per minute to approximately 250 P-waves per minute. In that the signal is sensed from electrodes which are "floating" in the atrium of the heart, it is possible that several P-waves in a row may go undetected and then capture is again regained. To preclude this from occurring, the averaging circuit employed includes a threshold level that responds such that the effect of 0 to 50 P-waves per minute is diminshed.

The second of the conditions listed above, i.e., that of always returning the pulse generator pacing rate to the lowest allowable rate, is accomplished by using a differentiating network incorporating a time constant of approximately 10 minutes. This allows a change in the P-wave averaged rate to be used to produce a corresponding change in the ventricular rate, but will always try to return the pacing rate to the lowest allowable preset rate in a time interval of approximately 30 minutes.

By using the system of the present invention in combination with a conventional R-wave inhibited demand pacemaker, the existing cardiac demand effectively controls the cardiac output by detecting the fundamental period of the atrial electrical cycle and using the changes in this period averaged over a 1.5 minute time span to raise and lower the ventricular heart rate to increase and decrease to cardiac output and in such a fashion that the control circuit strives to return the ventricular rate to a pre-established resting rate over a 30 minute time cycle. The system of the present invention thus comprises a first order control system satisfying the fundamental requirements of a true physiologically compatible pacemaker. The relationship of cardiac output being equal to cardiac demand in the present system will satisfy the physiological intent of the biological system of the body, provided a proper choice of circuit operating parameters are chosen.

OBJECTS

It is accordingly a principal object of the present invention to provide a new and improved cardiac stimulating system.

Another object of the invention is to provide a cardiac stimulating system in which cardiac output is made to track cardiac demand.

A still further object of the invention is to provide a control network for a conventional demand inhibited pulse generator whereby the rate at which pacer pulses are produced is determined by changes in a trial electrical activity rather than by the atrial events (P-wave occurrences) themselves.

A yet still further object of the invention is to provide a cardiac pacing system which closely emulates the physiological responses of the heart to changes in metabolic need.

A yet further object of the invention is to also provide means for adapting the stimulating rate of a cardiac pacer to the metabolic demands of the body patients where the normal conduction system of the heart is defective.

A still further object of the invention is to provide an electronic circuit which may be simply adjusted on an adaptive basis to changes in cardiac demand as reflected by changes in atrial electrical activity.

It is still a futher object of the invention to provide a device of very simple construction, which is highly reliable and consumes very little electrical energy so that it may be implanted in the body of the patient.

Other objects and advantages of the invention will appear from reading the following description of the invention, with reference to the accompanying drawings.

DESCRIPTION OF THE DRAWINGS

FIGS. 2a and 2b are a schematic electrical diagram of the controller circuits used to control a conventional demand/inhibited pulse generator in accordance with the present invention;

FIG. 2 shows how FIGS. 2a and 2b are connected; and

DESCRIPTION OF THE PREFERRED EMBODIMENT

Figures 1, 3:
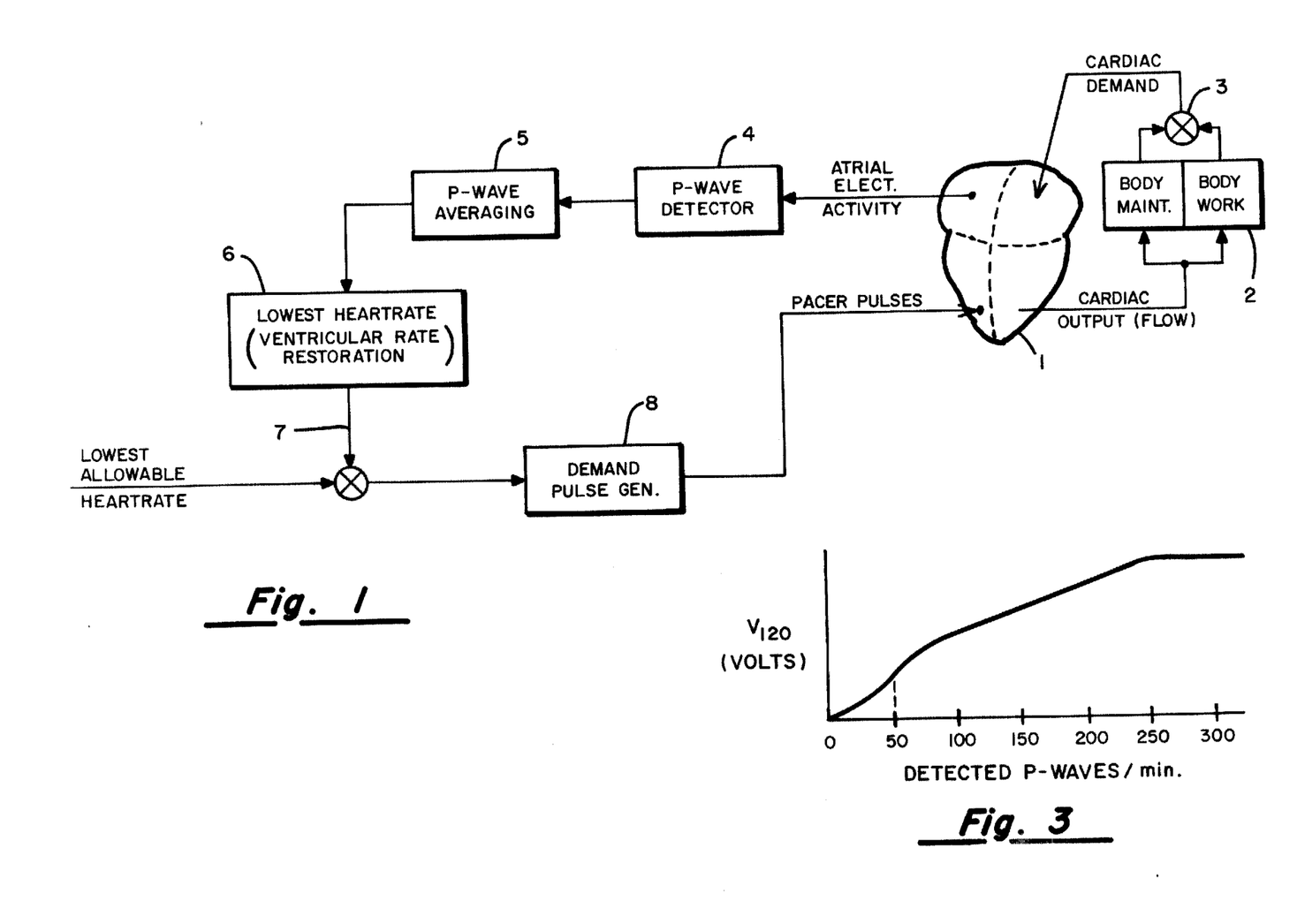
FIG. 1 is a general block diagram of the preferred embodiment.
FIG. 3 is a curve illustrating the transfer function of the controller network of FIG. 2b.

Referring first to FIG. 1, the general arrangement of the present invention will be set forth. Indicated by numeral 1 is a heart organ which is divided into its four chambers by the dotted lines. The heart, of course, is a pump for circulating blood and the cardiac output is generally equal to the stroke volume of the heart multiplied by the heart rate. This cardiac output or flow is shown as being delivered to the body identified by numeral 2. A first portion of the cardiac output is needed to supply adequate nutrition of cells and to maintain the internal environment of the body. Another portion of the cardiac output is required by certain organs to perform work. These two components combine in the body's metabolic system indicated schematically by numeral 3 and present chemical, electrical and possibly other inputs to the atrium of the heart. Cells in the SA node initiate the electrical impulse resulting in contraction. The impulse progresses as a wave over the atria and reaching the AV node. From there, the wave progresses through the atrioventricular bundle to the ventrical. In patients suffering from second or third degree heart block there is no longer a one-to-one relationship between atrial contractions and ventricular contractions. The atria will continue to contract at the rate established by the nerve impulses, but the ventricles may adopt a slower rate.

In the normal heart, all groups of muscle fibers in the atria and the ventricles contract in almost simultaneous phase. This forces blood out of the atria and into the ventricles, followed by ventricular contraction, which forces blood into the pulmonary artery and the aorta. In cases of atrial fibrillation, the muscle fibers of the atria contract almost continuously and asynchronously. In consequence, the muscles of the atria undergo irregular twitchy movements. More importantly, this means that the AV node is stimulated in an irregular fashion so that the ventricles contract normally, but with a completely irregular rhythm.

Even in patients suffering from second or third degree heart block and even in instances where atrial fibrillation is in progress, changes in the body's metabolic need still reflect changes in the atrial electrical activity. A sensing electrode on a lead disposed in the right atrium of the heart detects electrical signals, principally P-waves, and they are routed through the lead to a P-wave detector circuit 4. The detector circuit may include a band-pass filter for discriminating against electrical artifacts, other than P-waves, and for thresholding and shaping the signals emanating from the band-pass filter. The resulting signals are applied to an averaging circuit 5 which comprises an integrator network driven by a pulse generator, whereby predetermined measures of charge are stored in a capacitor associated with the integrator circuit of the P-wave averager 5. A resistive discharge path is also associated with that capacitor such that it tends to lose charge with a time constant of approximately 30 seconds. As a result, the output from the averaging circuit 5 is a voltage which is related to the number of P-waves sensed over approximately the preceding three time constant intervals or, typically, 1.5 minutes. This signal is applied to the ventricular rate restoration circuit 6 which, in the preferred embodiment, comprises a differentiating network which incorporates a relatively long time constant, typically 10 minutes. As such, the circuit 6 allows a change in the P-wave averaged rate to be used to produce a corresponding change in the ventricular rate, but it will always operate in a direction to return the ventricular rate to the lowest allowable rate in approximately 30 minutes. The signal appearing on line 7 may then be a current which is proportional in amplitude to changes in the P-wave rate. By applying this signal to a timing element in a conventional R-wave inhibited demand pacemaker its normal pacing rate of that device is made to deviate from its preset lowest allowable heart rate. In the block diagram of FIG. 1, the demand pulse generator is identified by numeral 8. It may, for example, comprise a Model 0503 MINILITH™ cardiac pacer manufactured by Cardiac Pacemakers, Inc. of St. Paul, Minn., the assignee of the instant patent application. For those desiring information on the details of construction and operation of that pulse generator, reference is made to the Anderson et al U.S. Pat. No. 4,041,953 which is assigned to the assignee of the instant application. The manner in which the control circuitry ties into that demand/inhibit cardiac pacer will be set forth in greater detail hereinbelow when the specifics of the construction of the overall system are described.

The output pulses from the demand, R-wave inhibited pulse generator 8 are applied through a lead to a further electrode disposed in the ventricle of the heart. In practice, the atrial sensing electrodes and the ventricular stimulating electrode may be disposed on a common lead such that only a single catheter need be routed through the vascular system and into the heart to obtain the sensed atrial signals, the sensed ventricular signals and to stimulate the ventricle.

With the foregoing organization and operating principles is mind, consideration will now be given to the details of the implementation of the preferred embodiment wherein the inventive aspects may be realized in an actual working circuit.

Figures 2, 2A:
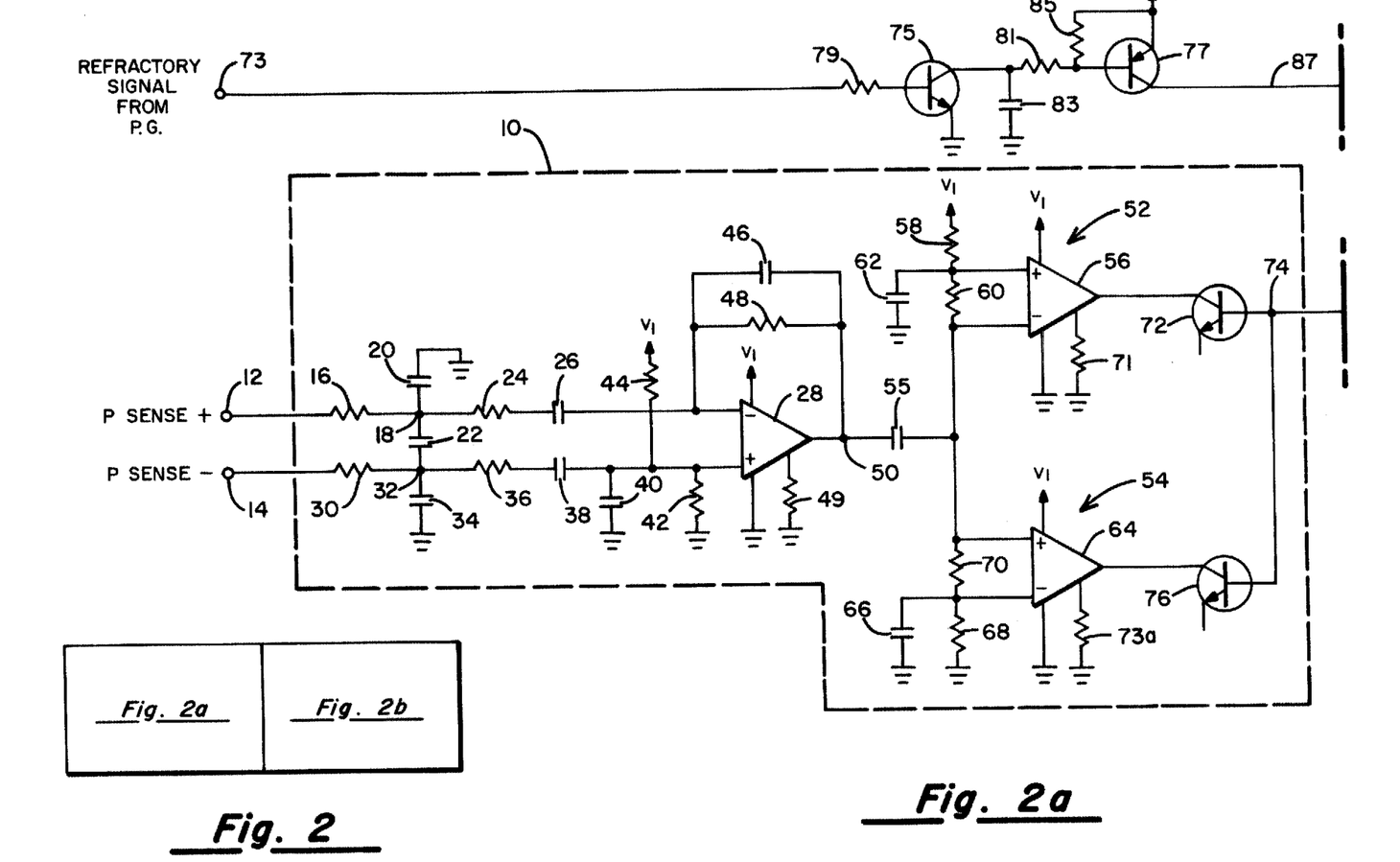
Figure 2B:
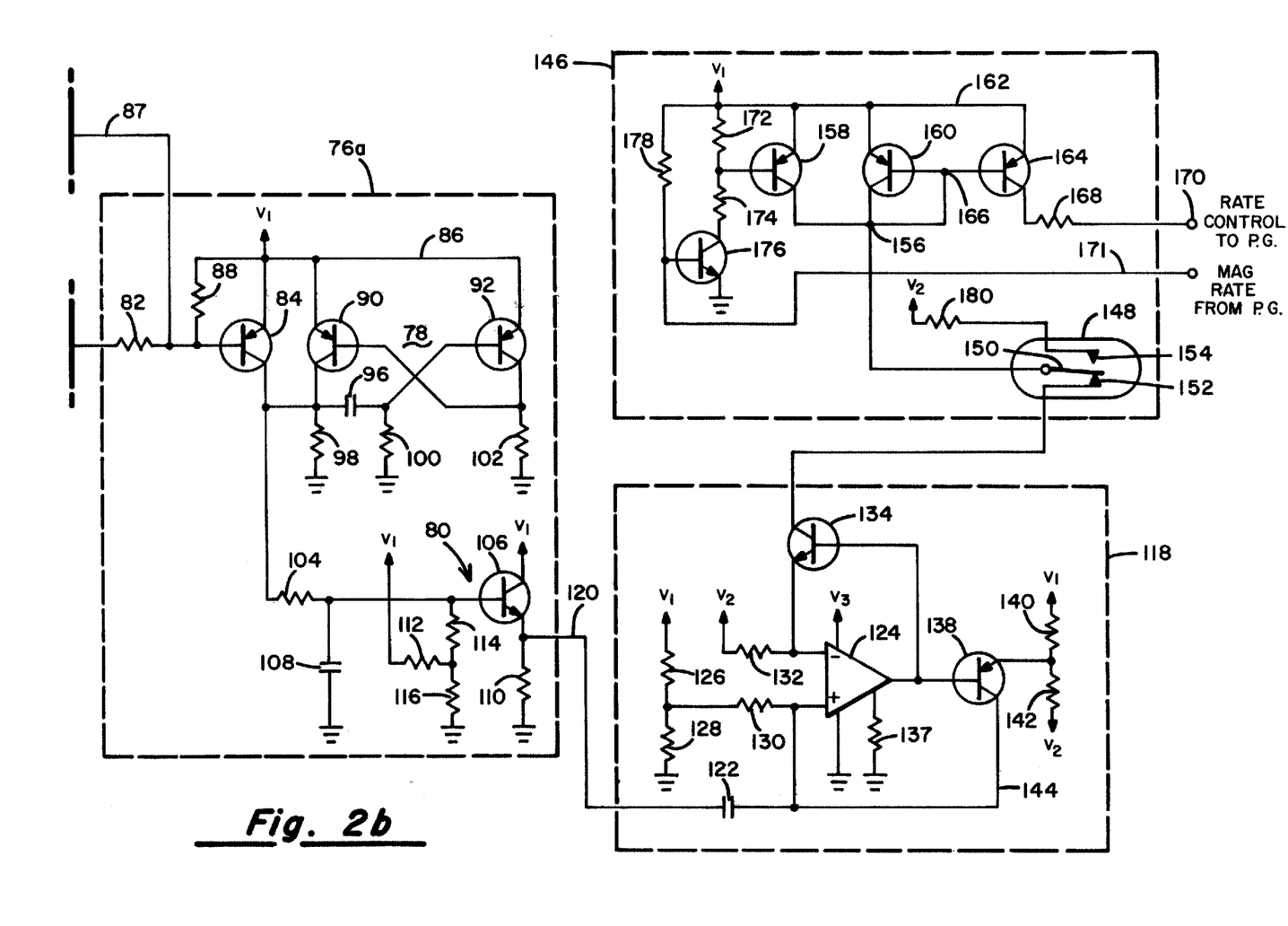

Referring then to FIGS. 2a and 2b, there is shown a preferred embodiment of a circuit capable of sensing changes in physiological demand and for producing a control signal which, when applied to a conventional demand pacemaker, will cause the pacing rate of the stimulating pulses applied to the ventricle to change as a function of physiological demand. Shown enclosed by dashed line box 10 is a P-wave sensing circuit which is adpated to have its input terminals 12 and 14 coupled to electrodes disposed proximate the high atrial wall of the patient so as to sense electrical signals corresponding to P-wave activity in the atrium. The electrode terminal 12 labeled P SENSE + is coupled through a resistor 16 to a junction 18 to which is connected a first terminal of a capacitor 20, a capacitor 22 and a resistor 24. The remaining terminal of the capacitor 20 is connected to circuit ground while the resistor 24 has its other terminal coupled through a capacitor 26 to the inverting input of an operational amplifier 28. The input terminal 14 labeled P SENSE — is likewise coupled through a resistor 30 to a junction point 32. The other terminal of the capacitor 22 is coupled to this junction point as is a first terminal of a further capacitor 34 and a resistor 36. The other terminal of the capacitor 34 is connected to circuit ground and the remaining terminal of the resistor 36 is coupled through a capacitor 38 to the non-inverting input of the operational amplifier 28. The non-inverting input of the operational amplifier 28 is also coupled through a further capacitor 40 to ground and a resistor 42 is coupled in parallel therewith. A predetermined bias is applied to the non-inverting input by way of a resistor 44 which is adapted to be connected to a source of regulated voltage $V_1$.

The operational amplifier 28 has a feedback circuit including a parallel combination of a capacitor 46 and a resistor 48 connected between its output junction 50 and the inverting input of the amplifier. The component values of the resistors and capacitors thus far identified are selected so as to cause the operational amplifier 28 to function as a band-pass filter whose center frequency corresponds to the predominant frequencies of received P-wave signals, yet providing relatively high attenuation of frequency components above and below that center frequency.

The output from the band-pass filter appearing at the junction 50 is connected as a first input to a set of comparators indicated generally by numerals 52 and 54. As can be seen from the drawing, the comparator 52 comprises an operational amplifier 56 having its inverting input connected by conductors to the junction 50. A regulated voltage $V_1$ is connected to a first side of a bias resistor 58 whose other side is connected to a junction tied directly to the non-inverting input of the operational amplifier 56. A resistor 60 is connected directly across the inputs to the operational amplifier 56 and a capacitor 62 is coupled between the non-inverting input thereof and circuit ground. With reference to the comparator 54, it too includes an operational amplifier 64 whose non-inverting input is connected directly to the junction point 50 at the output of the band-pass filter operational amplifier 28. The inverting input of the operational amplifier 64 is coupled to circuit ground via a parallel combination of a capacitor 66 and a resistor 68. A further resistor 70 is coupled directly across the input terminals of the operational amplifier 64.

The output from the operational amplifier 56 is coupled through a transistor 72 which is connected as a diode to a junction point 74. Similarly, the output from the operational amplifier 64 of the comparator 54 is coupled through a diode connected transistor 76 to the same junction point 74. Thus, the junction point 74 comprises a so-called "dot OR" of the respective outputs from the comparators 52 and 54. Thus, P-waves of either positive or negative polarity passing through the band-pass filter network and of an amplitude exceeding the threshold defined for the comparators 52 and 54 will cause an output pulse to appear at the junction point 74.

To preclude paced ventricular stimulating pulses which may feed back through the heart from adversely affecting the desired operation of the rate sensitive controller, an inhibiting circuit including the transistors 75 and 77 is included. The base of transistor 75 is adapted to be coupled through a resistor 79 to the conventional demand/inhibit pacer with which the controller hereof is adapted to be used. Specifically, and with reference to FIG. 6 of the aforereferenced Anderson et al U.S. Pat. No. 4,041,953, the refractory signal to be applied to the base of the transistor 75 may be obtained at the collector electrode of the transistor labeled Q103 in that figure. The emitter of NPN transistor 75 is tied to circuit ground and its collector is coupled through a resistor 81 to the base electrode of the transistor 77. A capacitor 83 is connected in parallel with the collector-to-emitter path of the transistor 75. A bias resistor 85 is connected between the voltage source $V_1$ and the base electrode of the transistor 77. The collector electrode of this last-mentioned transistor is connected by a conductor 87 to the output of the P-wave sensing circuit 10.

The portion of the circuit shown enclosed by dashed line box 76a may be considered as a frequency to voltage converter and includes as its operational elements a one-shot circuit indicated generally by numeral 78 and an integrator circuit indicated generally by numeral 80. Specifically, the dot OR junction 74 of the P-wave detecting circuit 10 is coupled through a resistor 82 to the base electrode of a PNP transistor 84. The collector electrode is connected to the rail 86 of the one-shot circuit which, in turn, is directly connected to the regulated voltage source $V_1$. A bias resistor 88 is connected between the source $V_1$ and the base electrode of the transistor 84. A pair of cross-coupled transistors 90 and 92 have their respective emitter electrodes connected to the rail 86 and the collector electrode of the transistor 90 is connected directly to the collector electrode of the transistor 84 at a junction 94. The collector electrode of the transistor 90 is coupled through a timing capacitor 96 to the base electrode of the transistor 92. The collector electrode of the transistor 92 is tied direclty to the base electrode of the transistor 90. A resistor 98 connects between the aforementioned junction point 94 and circuit ground. Likewise, a resistor 100 is connected between the base electrode of the transistor 92 and circuit ground. A further resistor 102 connects the common junction between the base electrode of the transistor 90 and the collector electrode of the transistor 92 to circuit ground.

The output from the one-shot circuit is coupled through a resistor 104 to the base electrode of a NPN transistor 106 forming a part of the integrating circuit 80. The integrating capacitor 108 is coupled between the base electrode of the transistor 106 and circuit ground. The emitter electrode of the transistor 106 is coupled through a resistor 110 to ground and its collector electrode is tied to the voltage source $V_1$. Bias is provided to the transistor 106 by way of a voltage divider including the resistors 112, 114 and 116. Specifically, the resistor 112 is connected at one side to the voltage source $V_1$ and its remaining terminal is tied in common with a first terminal of the resistors 114 and 116. The remaining terminal of the resistor 114 is connected to the base electrode of the transistor 106 while the remaining terminal of the resistor 116 is connected to circuit ground.

Shown enclosed by the dashed line box 118 is a current source controller circuit. As is illustrated, the output from the frequency to voltage converter circuit 76a appearing on line 120 which connects to the emitter electrode of the transistor 106 is coupled through a differentiating capacitor 122 to the non-inverting input of an operational amplifier 124. Also connected to this input is a voltage divider including series connected resistors 126 and 128 which are coupled between the regulated voltage source $V_1$ and circuit ground. The common junction between the resistors 126 and 128 is coupled through a further resistor 130 to a non-inverting input of the operational amplifier 124.

A further reference voltage $V_2$ is coupled to the inverting input of the operational amplifier 124 by way of a resistor 132. A NPN transistor 134 is employed as a feedback element for the operational amplifier and, in this regard, has its base electrode coupled to the output terminal 136 of the operational amplifier 124 and its emitter electrode tied to the inverting input of that amplifier.

With continued reference to the current source controller circuit 118, the output terminal 136 of the operational amplifier 124 is also connected to the base electrode of a PNP transistor 138 and the emitter electrode of that transistor is connected to a common point between two series connected resistor 140 and 142. The remaining terminal of the resistor 140 is connected to the voltage source $V_1$ whereas the remaining terminal of the resistor 142 is arranged to be connected to the voltage source $V_2$. The collector electrode of the transistor 138 is coupled via conductor 144 to the non-inverting input of the operational amplifier 124.

The current source itself is shown enclosed by the dashed line box 146 and is adapted to be coupled to the current source controller 118 by way of a bistable magnetic reed switch 148. When a permanent magnet is brought into proximity of the switch 148 with its north pole properly oriented, the switch arm 150 will be brought into contact with the contact 152 and it will remain in this position once the permanent magnet is again removed. To switch the magnet reed switch 148 to its opposite state, the polarity of the magnet is reversed as it is brought into proximity of the magnetic reed switch causing the switch arm 150 to move into contact with the contact 154. Again, when the permanent magnet is removed from a position in proximity to the reed switch, the switch arm 150 will remain in contact with the contact 154.

When the switch arm 150 abuts the contact 152, the system is said to be operating in its atrial rate sensitive mode. When the magnetic reed switch is operated such that its switch arm 150 contacts the contact 154, the system will be operating as a conventional ventricular demand pacemaker.

Assuming that the magnetic reed switch has been operated to its atrial rate sensitive mode position, the collector electrode of the transitor 134 will be connected to a junction point 156 in the current source circuit 146. The current source circuit includes a pair of PNP transistors 158 and 160 each having its collector electrode ties to the common junction point 156 and its emitter electrode tied to the rail 62 which, in turn, is connected to the voltage source $V_1$. A further PNP transistor 164 has its emitter tied to the rail 162 and its base electrode tied to a common junction 166 between the base electrode of transistor 160 and the junction point 156. The collector electrode of the transistor 164 is coupled through a resistor 168 to a terminal 170 which is adapted to be connected to a point in the constant current circuit of the demand cardiac pacer providing current to the pulse generator's timing capacitor. Typically, the terminal 170 may be connected to the common point between the collector electrode of transistor Q101 and the emitter electrode of transistor Q102 in the pacer circuit illustrated in FIG. 6a of the Anderson et al U.S. Pat. No. 4,041,953.

Bias voltage is applied to the base electrode of the transistor 158 by way of a resistor 172 which is coupled between the rail 162 and the base electrode of the transistor 158. A further resistor 174 is coupled between the base electrode of the transistor 158 and the collector electrode of a NPN transistor 176. The emitter electrode of this last-mentioned transistor is connected directly to circuit ground and its base electrode is coupled through a resistor 178 to the positive rail 162.

When the magnetic reed switch 148 is in its other position with the switch arm 150 abutting the contact 154, the connection between the output of the current source controller 118 and the current source 146 is broken and, instead, a resistor 180 is connected between the voltage source $V_2$ and the aforementioned junction point 156.

OPERATION—FIG. 2

As was already indicated, the input terminal 12 and 14 are adapted to be connected to sensing electrodes disposed in the upper right atrium of the heart. Typically, electrical activity applied to these terminals will include P-waves, R-waves, T-waves, signals relating to muscle artifact and possibly other noise picked up by the sensing electrodes. These signals are brought into the P-wave filter and detector 10 which includes a band-pass filter comprising the operational amplifier 28 and its associated input and feedback resistors and coupling capacitors. Component values are chosen so that the band-pass filter will respond primarily to P-waves and will attenuate other signals. The operational amplifier 28 is selected so as to exhibit relatively high common mode rejection, typically 30 db or more of the midband signals. The circuit components are chosen so that the band-pass filter will have a center frequency of approximately 20 Hz with upper and lower cut-off points at approximately 40 Hz and 10 Hz, respectively. The capacitors 20, 22 and 34 provide the desired high frequency rejection and tend to eliminate frequency components above around 100 Hz. The low frequency rejection of the band-pass filter is controlled primarily by capacitors 26 and 38 while capacitors 46 and 40 primarily control the low pass characteristics of the filter.

The operational amplifier 28 is arranged to provide a gain of approximately 100, the gain being determined primarily by the ratio of the value of resistor 48 to the sum of the values of resistors 16 and 24. This relationship holds true in that the component values associated with the non-inverting input to the operational amplifier 28 are matched to those associated with the inverting input of that amplifier.

The output from the band-pass filter appearing at junction 50 is applied to the input of threshold comparators 52 and 54 by way of a coupling capacitor 55. In that the signal is applied directly to the non-inverting input of the amplifier 64 and to the inverting input of amplifier 56 in the manner indicated, the battery voltage $V_1$ is applied across the voltage divider network including resistors 58 and 60 and resistors 70 and 68. This establishes the DC level or threshold for the comparators. The incoming signal from the operational amplifier 28 when no input signal is being impressed upon the terminals 12 and 14, results in the comparator amplifiers 56 and 64 producing an output signal that is "high", i.e., near the power supply level. If a received P-wave is positive, amplifier 56 will produce a low output while the output of amplifier 64 will remain in the high state. However, if the input P-wave signal exhibits a negative excursion, then the reverse would be true. Specifically, a negative going signal exceeding the threshold established will cause the comparator 64 to output a low output while the output of amplifier 56 will remain in the high state.

The transistors 72 and 76 are connected as diodes and because of the manner in which their bases are tied together at the common junction 74, an OR logic function results. The use of transistors 72 and 76 instead of conventional diodes provide a lower forward voltage drop when conducting than would otherwise be obtainable. Appearing at the junction 74, then, will be low going pulses or spikes corresponding to sensed signals in the atrium which are of the proper frequency to pass through the band-pass filter and of an amplitude sufficient to satisfy the criteria established for the comparators 52 and 54. The spikes are coupled through the resistor 82 to the base electrode of the transistor 84. Upon the occurrence of each spike, that base electrode is driven low, momentarily causing the transistor 84 to conduct such that its collector goes high to trigger the one-shot circuit comprised of the cross-coupled transistors 90 and 92. This drives the one-shot to its metastable state where it remains for a period determined primarily by the RC time constant determined by the resistor 100 and the capacitor 96. In the preferred embodiment, this time period is set to be 150 milliseconds and is a square wave of a predetermined amplitude. The 150 millisecond pulse width is not critical.

At this point, it is appropriate to describe the operation of the inhibiting circuit comprised of the transistors 75 and 77. The terminal 73 is arranged to be coupled to the demand, R-wave inhibited pacer at a point at which the refractor signal of that device goes positive at the onset of the generation of a pacer pulse or when a naturally occurring R-wave signal is sensed by that pacer. The onset of the refractory pulse causes the transistor 75 to become conductive and the current flow through the resistors 85 and 81 from the source $V_1$ causes a negative signal to be applied to the base of transistor 77 turning it on. Once transistor 77 is conductive, the output from the P-wave filter/detector network 10 is held high preventing the output from the network 10 from triggering the one-shot circuit 78. The time period that the conductor 87 carries its high signal is determined by the component values of the resistors 81 and 85, the capacitor 83 and transistor 77. By setting this to approximately 80 milliseconds, it has the capability of precluding natural or paced R-waves or PVC's from firing the one-shot circuit. The inhibiting circuit just described, then, is effective to preclude R-waves (paced or natural) as well as certain other artifacts from affecting the operation of the averaging circuit including the one-shot circuit 78 and the integrator network 80 which it drives. The P-wave averager 76a will be precluded from receiving paced R-waves and sensed R-waves that occur simultaneously in both the ventricle and the atrium. However, if there is a delay greater than 80 milliseconds as established by the sum of resistors 81 and 85 and the capacitor 83, the one-shot circuit 78 will be triggered. This leaves the P-waves as the predominant event for triggering the one-shot 78.

Upon each triggering of the one-shot, the integrating capacitor 108 will be fed an increment of charge determined by the width and amplitude of the output pulse from the one-shot circuit and the magnitude of the coupling resistor 104. The resistors 112, 114 and 116 effectively establish a DC voltage quiescent level upon which the output from the one-shot circuit rides. It is to be further noted that there is an additional discharge path for the integrating capacitor 108. Specifically, it consists of the resistors 104 and 98 back in the one-shot circuit 78. Hence, if no energy at all is being transmitted into this capacitor 108, i.e., the one-shot remains at its base level and no P-waves are being detected, the voltage at the base of transistor 106 will be set by the voltage derived from the source $V_1$ which is fed through the resistors 112, 114 and 116.

For each P-wave that causes the one-shot circuit to be triggered, it will result in a small quantity of charge being dumped into the integrating capacitor 108. Assuming for the moment that only a single pulse from the one-shot 78 occurs during a long time interval, the capacitor 108 will discharge through the path including resistors 104 and 98 as well as through the path including resistors 114 and 116. These resistors are selected such that the time constant will be approximately 30 seconds. Given an increase in voltage on the capacitor 108 due to the triggering of the one-shot, that voltage will increase but it will then decrease. At the end of approximately three time constants, i.e., typically about 1½ minutes, the capacitor voltage will have decayed back to its quiescent level. However, if the number of P-waves sensed increases from 0 to some greater number, the voltage on the integrating capacitor 108 will build up in steps in that charges being added to it at a rate greater than what is being removed from it. Thus, the voltage on the capacitor is related to the rate at which P-waves are received. The circuit is designed such that when the P-wave rate reaches approximately 250 bpm, the voltage on the capacitor will cease to increase. With reference to FIG. 3, then, the dynamic range of the system can be represented graphically as indicated. It is important to a clear understanding of the operation of the present invention that it be realized that the system of the present invention is sensitive to changes in P-wave rates and not merely to the occurrence of the P-wave itself as is the case with certain prior art pacers of the P-synchronous type.

Referring to FIG. 3, if the detected P-wave rate is approximately 70 bpm and because of the physiologically induced change, the P-wave rate increases or decreases, say, 5 bpm, then the voltage across the capacitor 108 will vary slightly above and below the value existing at the 70 bpm value. Likewise, if the atrial rate is running at 200 bpm and again due to a change in physiologic demand there is an incremental increase of 5 bpm, the voltage change across the capacitor 108 will be about the same as it was for a 5 bpm change centered around the 70 bpm level.

Furthermore, it is to be recognized that with a typical lead having atrial sensing capabilities, the lead is free, within limits, to move about within the atrium. As such, it may sometimes be in direct contact with the heart and other times it will not be. This results in the possibility for massive fluctuations of the signal levels. It is thus possible to get jumps from, say 0 bpm being detected to around 70 bpm just by virtue of lead movement. By providing a less sensitive zone on the transfer characteristic from 0 to 50 bpm, changes due to lead displacement are effectively minimized.

After the control voltage which is proportional to the sensed P-wave rate is developed at the emitter electrode of the transistor 106, it is further processed by the current controller circuit 118 in such a fashion that only changes in the P-wave rate are of significance. The changes in atrial rate, of course, are dependent upon physiologic demand of the body.

The capacitor 122 in combination with the remainder of the circuit provides a very large time constant, the capacitor acting as a differentiator. Stated otherwise, it comprises a high pass filter with an extremely long time constant. The time constant is determined by the value of the capacitor 122 in microfarads multiplied by the effective resistance of resistors 126, 128 and 130 measured in megohms. This time constant may be set to be approximately in the range of from 5 to 35 minutes, 10 minutes being typical. Under steady state conditions, the voltage appearing at the positive input of the amplifier 124 will be determined by the magnitude of the DC voltage $V_1$ applied through the resistor network including resistors 126, 128 and 130. The capacitor 122 will allow only changes in the integrated voltage to pass. These high frequency components consist of any changes that are observed in the control voltage developed at the emitter of transistor 106. With the time constant chosen, upon the occurrence of a sudden change in the input, approximately 30 minutes, i.e., approximately three time constants, are required for the control voltage to return to its quiescent or steady state level. This 30 minute period corresponds quite closely to that which matches human physiological requirements. That is to say, following significant exercise, approximately 20 to 30 minutes are required for the heart rate to return to the at rest rate.

It is to be noted, then, that the averager circuit 76 provides a time constant in the range of from 15 to 45 seconds, about 30 seconds being preferred in that it yields approximately a 1½ minute window corresponding to normal physiologic increases of the cardiac rate. As mentioned, the differentiator, including the large capacitor 122, may have a time constant of approximately 10 minutes, defining a 30 minute window, in which the control voltage returns to its quiescent level following the change which it experienced.

The control signal which is developed at the non-inverting input of the amplifier 124 is the actual control signal which is, at this point, a function of the changes in P-wave rate, not the absolute value of the P-wave rate. The amplifier 124 is designed to convert that control signal into a current which may be injected into a conventional R-wave inhibited demand pacer in such a fashion that the rate at which ventricular stimulating pulses are generated will be adjusted as a function of that control signal. Referring momentarily to FIG. 6a of the Anderson et al U.S. Pat. No. 4,041,953, the transistors Q101 and Q102, along with the resistors R103 and R104, comprise a constant current generator. That current source sets up a voltage, then, that allows a current through transistor Q103 for charging up the pulse generator's timing capacitor C101. That last-mentioned capacitor forms a portion of the RC time constant of the oscillator portion of the pacer pulse generator. By injecting current at the point indicated, the charging time of the capacitor C101 is decreased and the ventricular stimulating pulses appearing cross the Heart + and the Heart − terminals will increase, assuming that naturally occurring R-waves do not inhibit the operation of that demand pacer.

When it is desired to use the physiologic demand control circuit of FIGS. 2a and 2b with a conventional, commercially available ventricular R-wave inhibited demand pacer, it may be desirable to provide a means whereby the physiologic control may be selectively disengaged to thereby allow the demand pacer pulse generator to operate in its normal fashion. To accomplish this end, a magnetic reed switch 148 of the bipolar type is provided. If a permanent magnet is brought into proximity of such a device with the magnet aligned in a first direction, the switch arm 150 can be made to abut a first one of the contacts 152 and 154. When the magnet is then taken away, the switch arm will remain in this orientation. However, when the permanent magnet is reversed so that its north pole is oriented in an opposite direction than before and again brought into proximity with the magnetic reed switch, it will revert to its opposite state and remain there when the permanent magnet is again removed. When the switch arm 150 abuts the contact 152, the system is in its so-called "rate-sensitive" or physiologic mode. However, when the switch arm 150 is made to abut the contact 154 the circuitry of FIGS. 2a and 2b is effectively removed from its cooperating relationship with the R-wave inhibited demand pacer circuit although it continues to process atrial electrical signals in the manner described.

Amplifier 124 is a standard operational amplifier with a gain control range that is established by a resistor 132 and the voltage source $V_2$. This voltage source causes a current to flow through the resistor 132 and away from the inverting input of the amplifier 124. This current is established by the difference of potential between $V_2$ and the voltage appearing at the inverting input of the amplifier. In accordance with standard operational amplifier theory, because of the assumed infinite input impedance existing between the operational amplifier's two inputs, the voltage at the inverting input must be exactly equal to that at the non-inverting input. Thus, the voltage at the non-inverting input is a representation of the detected and processed P-wave rate change. The amplifier 124 then sets up a current through the transistor 134 which is coupled back to the inverting input. As a result, the output from the operational amplifier 124 establishes a current through the base-emitter junction of transistor 134 causing the voltages at the inverting and non-inverting inputs to be equal to each other. The operational amplifier 124 then functions to establish a current through the transistor 134 to ensure that that relationship holds true. In that the transistor 134 is chosen to have a very high gain, its collector current is effectively equal to the base-emitter current which it carries. The collector current, then, flows through the closed magnetic reed switch to the bases of the transistors 160 and 164. The collector current of transistor 160 is thus equal to the current flowing through the emitter of transistor 134. As transistors 160 and 164 are matched, it can be seen that the current flowing out of the collector of the transistor 164 must be equal to the current flowing through the resistor 132 to the reference source $V_2$ and is therefore proportional to the control voltage. It is this collector current which flows through the resistor 168 which is ejected into the point previously indicated on the R-wave inhibited demand pacer.

The resistor 168 in the collector circuit of transistor 164 provides a safety feature. It is chosen such that the maximum current which can be injected will not cause the ventricular pacer stimulating pulses to be generated at a rate greater than a predetermined maximum, e.g., 130 bpm.

A commercially available pacer pulse generator with which the physiologic controller of the present invention may be used includes a so-called "mag rate" feature for determining battery status. Again, by bringing a permanent magnet close to the implanted pacer, a magnetic reed switch is closed, causing the pacer to revert to its asynchronous mode wherein the frequency of the output pulses provides a measure of the state of depletion of the battery power source. This feature is more particularly explained in the Anderson et al Patent previously cited. In order to still obtain that type of operation, a connection is established via line 171 to the "mag rate" terminal depicted in FIG. 6a of the Anderson et al Patent. When the pacer is placed in its mag rate, the base of the transistor 176 is no longer grounded causing transistor 176 to conduct which, in turn, turns on the transistor 158. With this latter transistor conducting, the current mirror transistors 160 and 164 are turned off and no control current can be injected into the timing capacitor of the ventricular pulse generator's oscillator. It is to be noted, however, that the turning off of the control current delivered to the pacer's oscillator does not inhibit the controller of FIG. 2 from continuing to monitor atrial electrical activity and developing the appropriate control signal proportional in amplitude to changes in the P-wave rate. As soon as the permanent magnet governing the mag rate operation is removed, the current supply to the pacer's timing capacitor will be restored.

When the bipolar magnetic reed switch 148 is operated to cause the switch arm 150 to abut the contact 154, the demand inhibited pacer will operate in its conventional fashion without being controlled on the basis of atrial activity. That is to say, the current line leading from the collector of the transistor 134 to the current mirror comprises of the transistors 160 and 164 is opened. A current passes to the source $V_2$ through the current limiting resistor 180 and through the magnetic reed switch to the current mirror such that a fixed or steady current is injected into the R-wave inhibited pacer. By providing this steady injected current, desired pacing rate is provided. That is to say, when operating in its physiological mode, the basic lowest pacing rate which the pacer is allowed to produce is arranged to be somewhat lower than what would normally be established when the system is functioning strictly as a demand/inhibit pacer. Hence, if a patient is asleep, his pacer can slow down to, say, 60 bpm and reliance is placed upon the physiologic demand to increase the pacer rate from that lowermost value. However, when the system is operating in strictly the R-wave inhibited pacer mode, it is typical that its pacing rate be somewhere around 75 bpm. By drawing a small, fixed quantity of current to the voltage source $V_2$ through the current limiting resistor 180 and through the magnetic reed switch to the current mirror transistors 160 and 164 and from there through the resistor 168 to the timing capacitor of the demand/inhibit pacer, it raises the base pulse rate from the lower value to a slightly higher value corresponding to normal R-wave pacer operation.

With continued reference to FIG. 2b, the transistor 138 and its associated bias resistors 140 and 142 act as a voltage clamp for the operational amplifier 124. The purpose of providing this clamp will now be explained. Normally, whenever a rapid rate change is detected, it operates to raise or lower the ventricular stimulating rate correspondingly. However, if the system happens to be operating at a fairly nominal ventricular rate, for example 80 bpm, and suddenly capture is lost and the change in the P-wave rate drops drastically, the pacer will ultimately return to its lower rate limit. Since the differentiator responds to changes in either direction, this loss of sensing would reduce the ventricular paced rate to the established lower rate limit. Indeed, the control voltage on the non-inverting amplifier input could be driven below the bias point set by reference voltage $V_2$. Since the feedback element in the inverting loop of the operational amplifier 124 is an NPN transistor, i.e., transistor 134, this state cuts off the injected current to the R-wave inhibited pacer pulse generator and turns on clamping transistor 138 which then supplies the necessary current needed to restore the non-inverting input to the reference set by $V_2$. The effect of this action is to produce a hysteresis characteristic to the long time constant created by the differentiator comprises of capacitor 122, resistors 126, 128 and 130. This hysteresis is based on the direction and magnitude of the atrial activity rate change. The non-inverting input of the operational amplifier 124 is also biased by resistors 126, 128 and 130 such that in the quiescent state, the control signal, based on the change in the atrial activity, is zero. The clamp transistor 138 is turned on slightly, thus ensuring that transistor 134 is turned off and the pacer pulse generator is in its base rate.

An absolute limit on the amount of current which may be injected into the timing capacitor in the R-wave inhibited pacer is set by resistor 168. As more current is delivered to the pacer through this resistor, the voltage drop across this resistor increases to a point where the collector current of transistor 164 no longer mirrors a collector current of transistor 160, but rather is limited to a maximum level that corresponds to the specified upper rate limit of the spaced ventricular frequency, typically 135 bpm.

The following table sets forth typical component values which may be used in implementing the present invention. It is to be understood, however, that the values indicated are illustrative and not limitative.

TABLE I

| Component(s) Resistors | Value(s) |
| --- | --- |
| 16, 24, 30, 36 | 47 K |
| 42, 44 | 24 M |
| 48, 114 | 12 M |
| 49, 137, 174 | 22 M |
| 58, 68 | 10 M |
| 60, 70 | 220 K |
| 71, 73a, 85, 100, 102, 104 | 20 M |
| 79, 132 | 1 M |
| 81 | 5 M |
| 82, 98, 110, 142 | 2 M |
| 88, 172, 178 | 30 M |
| 112 | 13 M |
| 116 | 7.5 M |
| 126 | 25 M |
| 128 | 14 M |
| 130 | 7.9 M |
| 140 | 5.1 M |
| 168 | 7.1 M |
| 180 | 18 M |
| Capacitors | |
| 20, 34 | 0.0015 microfarads |
| 26, 38 | 0.15 microfarads |
| 40, 36 | 220 picofarads |
| 62, 66 | .068 microfarads |
| 83, 96 | .01 microfarads |
| 108 | 3.3 microfarads |
| 122 | 33 microfarads |
| Transistors | |
| 72, 75, 76, 106, 134, 176 | 2N2484 |

TABLE I-continued

| Component(s) Resistors | Value(s) |
| --- | --- |
| 77, 84, 90, 92, 138, 158, 160, 164 | 2N3799 |
| Op. Amps | |
| 28, 56, 64, 124 | Type 4250 |

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself.

What is claimed is:

1. Cardiac stimulating apparatus having means for adjusting the frequency of stimulation as a function of physiologic demand, comprising in combination:
    (a) a pulse generator having timing means therein for determining the frequency at which cardiac stimulating pulses are produced;
    (b) detector means for detecting natural atrial electrical activity characteristic of physiologic demand and producing trigger signals in response to said natural atrial electrical activity;
    (c) averaging means coupled to receive said trigger signals for developing a voltage related to the rate of occurrence of said trigger signals during predetermined time intervals;
    (d) circuit means coupled to said averaging means and responsive to said voltage for generating a control signal proportional in amplitude to changes in said voltage; and
    (e) means for applying said control signals to said timing means in said pulse generator to thereby alter the said frequency at which stimulating pulses are produced.
2. The cardiac stimulating apparatus as in claim 1 wherein the stimulating pulse frequency is variable between a lower rate limit and upper rate limit in response to said control signal.
3. The cardiac stimulating apparatus as in claim 2 wherein said timing means, in the absence of said control signal, causes the stimulating pulse frequency to be at said lower rate limit.
4. The cardiac stimulating apparatus as in claim 2 wherein said control signal decreases to a predetermined quiescent level within a further time interval which is relatively long compared to said predetermined time interval when said voltage from said averaging means in unchanging, said quiescent level corresponding to said lower rate limit.
5. Cardiac stimulating apparatus having means for adjusting the frequency of stimulation as a function of physiologic demand, comprising in combination:
    (a) a pulse generator having timing means therein for determining the frequency at which cardiac stimulating pulses are produced;
    (b) means coupled to receive signals representing natural atrial P-waves for producing a control signal related in amplitude to changes in P-wave frequency; and
    (c) means for applying said control signal to said timing means in said pulse generator to thereby alter the said frequency at which stimulating pulses are produced.

* * * * *